United States Patent [19]

Rohr

[11] Patent Number: 4,871,753
[45] Date of Patent: Oct. 3, 1989

[54] 3-PHENYL-5-TRIFLUOROMETHYL-1,2,4-OXADIAZOLE COMPOUNDS WHICH ARE USEFUL PESTICIDES

[75] Inventor: Otto Rohr, Therwil, Switzerland

[73] Assignee: Ciba-Geigy Corporation, Ardsley, N.Y.

[21] Appl. No.: 130,833

[22] Filed: Dec. 9, 1987

[30] Foreign Application Priority Data

Dec. 12, 1986 [CH] Switzerland ............... 4948/86
Dec. 12, 1986 [CH] Switzerland ............... 4949/86
Oct. 22, 1987 [CH] Switzerland ............... 4134/87

[51] Int. Cl.$^4$ .......................................... C07D 271/06
[52] U.S. Cl. ........................................ 514/364; 548/131
[58] Field of Search ........................ 548/131; 514/364

[56] References Cited

U.S. PATENT DOCUMENTS

| | | | |
|---|---|---|---|
| 3,192,103 | 6/1965 | Sousa et al. | 514/340 |
| 3,227,725 | 1/1966 | Eloy et al. | 548/131 |
| 4,003,909 | 1/1977 | Narayanan | 548/131 |
| 4,069,332 | 1/1978 | Wright | 548/131 |
| 4,243,409 | 1/1981 | Schmidt et al. | 71/92 |

FOREIGN PATENT DOCUMENTS 2801509 7/1979 Fed. Rep. of Germany ...... 548/131
WO86/03941 7/1986 PCT Int'l Appl. .

OTHER PUBLICATIONS

Chemical Abstracts, Abstract No. 150674y, vol. 95, No. 17, Oct. 26, 1981 (Sumitomo Chemical).

Primary Examiner—Mary C. Lee
Assistant Examiner—Zinna Northington
Attorney, Agent, or Firm—Edward McC. Roberts

[57] ABSTRACT

Compositions containing as active component a compound of the formula

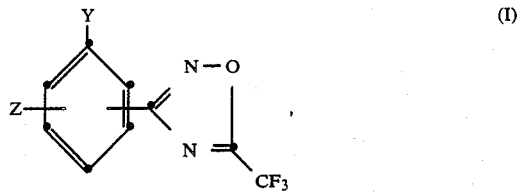

in which Y represents OR' or HNR" and Z represents hydrogen or $(R_4)_n$, and which covers, as sub-groups, the compounds of the formulae I' and I"

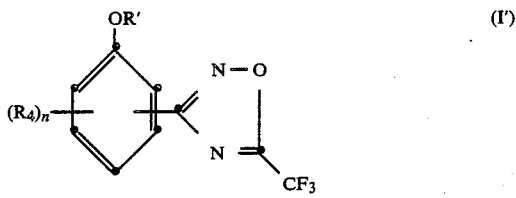

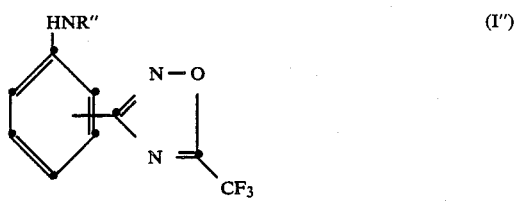

in which:
R' represents hydrogen, $C_1-C_4$-alkyl, aryl, substituted aryl, $C(X)NR_1'(R_2')$, $C(O)XR_3'$ or $COR_3'$;
$R_1'$ represents $C_1-C_9$-alkyl, $C_1-C_4$-alkoxy, $C_2-C_4$-alkenyl, aryl or substituted aryl;
$R_2'$ represents hydrogen or $C_1-C_4$-alkyl;
$R_3'$ represents $C_1-C_{15}$-alkyl, $C_2-C_4$-alkenyl or aryl;
$R_4$ represents halogen, $C_1-C_4$-alkoxy or nitro; and
n represents 0, 1 or 2;
X represents oxygen or sulphur;
R" represents $C(O)NR_1''(R_2'')$, $C(S)NR_1''(R_2'')$, $COOR_3''$, $COSR_3''$ or $COR_3''$;
$R_1''$ represents $C_1-C_4$-alkyl, $C_1-C_4$-alkoxy or aryl;
$R_2''$ represents hydrogen or $C_1-C_4$-alkyl and
$R_3''$ represents $C_1-C_9$-alkyl, $C_1-C_4$-haloalkyl, $C_3-C_4$-alkenyl or aryl;
including their acid addition salts.

The active ingredients have microbicidal properties and are suitable especially for controlling phytopathogenic microorganisms.

18 Claims, No Drawings

3-PHENYL-5-TRIFLUOROMETHYL-1,2,4-OXADIAZOLE COMPOUNDS WHICH ARE USEFUL PESTICIDES

The present invention relates to novel 3-phenyl-5-trifluoromethyl-1,2,4-oxadiazole derivatives and to pesticides that contain as active ingredient at least one compound of the formula I below or an acid addition compound thereof, to the preparation of those compounds or the compositions containing them and to methods of controlling pests, especially controlling or preventing attacks on plants by phytopathogenic microorganisms.

The active ingredients have the formula I

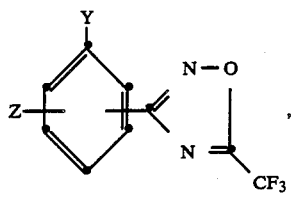
(I)

in which Y represents OR' or HNR'' and Z represents hydrogen or $(R_4)_n$, and which covers, as sub-groups, the compounds of the formulae I' and I''

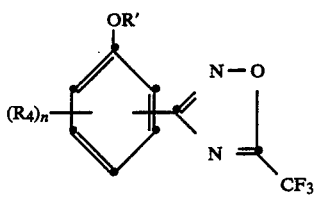
(I')

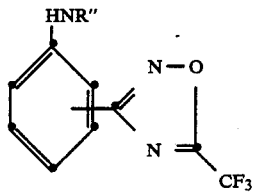
(I'')

in which:
R' represents hydrogen, $C_1$-$C_4$-alkyl, aryl, substituted aryl, $C(X)NR_1'(R_2')$, $C(O)XR_3'$ or $COR_3'$;
$R_1'$ represents $C_1$-$C_9$-alkyl, $C_1$-$C_4$alkoxy, $C_2$-$C_4$-alkenyl, aryl or substituted aryl;
$R_2'$ represents hydrogen or $C_1$-$C_4$-alkyl;
$R_3'$ represents $C_1$-$C_{15}$-alkyl, $C_2$-$C_4$alkenyl or aryl;
$R_4$ represents halogen, $C_1$-$C_4$-alkoxy or nitro; and
n represents 0, 1 or 2;
X represents oxygen or sulphur;
R'' represents $C(O)NR_1''(R_2'')$, $C(S)NR_1''(R_2'')$, $COOR_3''$, $COSR_3''$ or $COR_3''$;
$R_1''$ represents $C_1$-$C_4$-alkyl, $C_1$-$C_4$alkoxy or aryl;
$R_2''$ represents hydrogen or $C_1$-$C_4$-alkyl and
$R_3''$ represents $C_1$-$C_9$-alkyl, $C_1$-$C_4$-haloalkyl, $C_3$-$C_4$-alkenyl or aryl; including their acid addition salts.

Compounds of the formula I' are novel and some of the compounds of the formula I'' are novel.

Compounds of the formula Ia' constitute a preferred group:

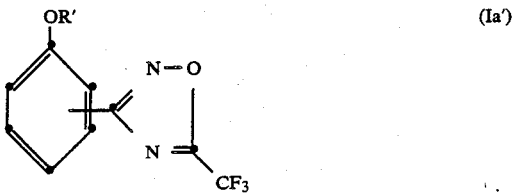
(Ia')

in which
R' represents hydrogen, $C_1$-$C_4$-alkyl, aryl, substituted aryl, $C(X)NR_1'(R_2')$, $C(O)XR_3'$ or $COR_3'$;
$R_1'$ represents $C_1$-$C_9$-alkyl, $C_1$-$C_4$alkoxy, $C_2$-$C_4$-alkenyl, aryl or substituted aryl;
$R_2'$ represents hydrogen or $C_1$-$C_4$-alkyl;
$R_3'$ represents $C_1$-$C_{15}$-alkyl, $C_2$-$C_4$-alkenyl or aryl; and
X represents oxygen or sulphur, including the acid addition salts thereof.

A further group comprises compounds of the formula I' in which n represents 1 or 2.

Compounds of the formula I'' in which the radical

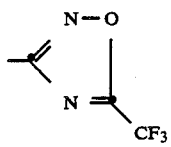

is in the 4-position of the phenyl ring and R'' has the meanings given under formula I'' are novel. These novel compounds, which fall within the scope of formula I'', are embraced by the formula Ia''

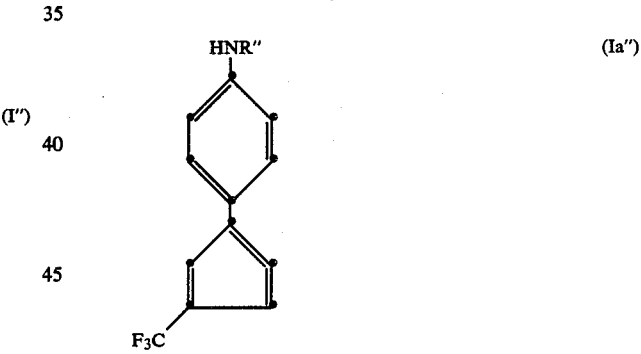
(Ia'')

in which R'' has the meanings given under formula I. The novel compounds of the formula Ia'' including their acid addition salts form part of the invention.

Depending on the indicated number of carbon atoms, alkyl by itself or as a moiety of another substituent should be understood as being a straight-chain or branched group, for example: methyl, ethyl, propyl, butyl, pentyl, hexyl, heptyl, octyl or nonyl to pentadecyl and the isomers thereof, such as, for example, isopropyl, isobutyl, tert.-butyl, sec.-butyl or isopentyl.

Alkenyl is, for example, propen-1-yl, allyl, buten-1-yl, buten-2-yl or buten-3-yl.

Halogen by itself or as moiety of another substituent is fluorine, chlorine, bromine or iodine, preferably fluorine, chlorine or bromine.

By aryl is meant phenyl or naphthyl, preferably phenyl. Suitable substituents of aryl are halogen, $C_1$-$C_4$-alkyl, especially methyl, or $C_1$-$C_2$-haloalkyl having from 1 to 3 halogen atoms, especially trifluoromethyl.

Suitable acids for forming acid addition salts with compounds of the formula I are any organic and inorganic acids provided they form plant-physiologically tolerable salts.

Examples of acid addition salt-forming acids are inorganic acids: hydrohalic acid, such as hydrofluoric acid, hydrochloric acid, hydrobromic acid or hydriodic acid, and also sulphuric acid, phosphoric acid, phosphorous acid and nitric acid, and organic acids, such as acetic acid, trifluoroacetic acid, trichloroacetic acid, porpionic acid, tartaric acid, glycolic acid, thiocyanic acid, lactic acid, succinic acid, citric acid, benzoic acid, cinnamic acid, oxalic acid, formic acid, benzenesulphonic acid, p-toluenesulphonic acid, methanesulphonic acid, salicylic acid, p-aminosalicylic acid, 2-phenoxybenzoic acid or 2-acetoxybenzoic acid. These acids are added to the relevant free compounds of the formula I in accordance with methods known per se.

The compounds of the formula I are stable at room temperature. They can be used in agriculture or related fields, especially preventively or curatively, for controlling plant-destructive microorganisms. The compounds of the formula I have very good fungicidal action and can be readily applied in a wide range of concentrations. In addition, the compounds have other pesticidal properties. For example, they can also be used to control nematodes, especially plant-destructive nematodes, and to control feeding and plant-destructive sucking insects.

Owing to their pronounced pesticidal, especially microbicidal, activity, the compounds of the formula Ia' that are especially preferred are those in which
(a) R' represents hydrogen, phenyl, substituted phenyl, C(X)NR$_1$'(R$_2$'), C(O)XR$_3$' or COR$_3$';
R$_1$' represents C$_1$–C$_9$-alkyl, C$_1$–C$_4$alkoxy, C$_2$–C$_4$-alkenyl or phenyl;
R$_2$' represents hydrogen or C$_1$–C$_4$-alkyl;
R$_3$' represents C$_1$–C$_{15}$-alkyl, C$_2$–C$_4$alkenyl or phenyl; and
X represents oxygen or sulphur, or
(b) the radical

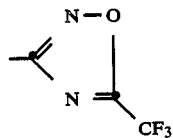

is in the 4-position of the phenyl ring, and which compounds at the same time have the following substituents or combinations of these substituents with one another:
R' represents hydrogen, phenyl, phenyl substituted by halogen or by methyl, C(X)NR$_1$'(R$_2$'), C(O)XR$_3$' or COR$_3$', in which R$_1$' represents C$_1$–C$_4$-alkyl, C$_1$–C$_2$-alkoxy, allyl or phenyl; R$_2$ represents hydrogen or C$_1$–C$_2$-alkyl; R$_3$' represents C$_1$–C$_9$-alkyl, C$_2$–C$_4$-alkenyl or phenyl; and X represents oxygen or sulphur;
or
R' represents hydrogen, C$_1$–C$_4$-alkyl, phenyl, substituted phenyl, C(X)NR$_1$'(R$_2$'), C(O)XR$_3$' or COR$_3$', in which R$_1$' represents C$_1$–C$_4$-alkyl, C$_1$–C$_4$-alkoxy, allyl or phenyl; R$_2$' represens hydrogen or C$_1$–C$_4$-alkyl; R$_3$' represents C$_1$–C$_9$-alkyl, C$_2$–C$_4$-alkenyl or phenyl; and X represents oxygen or sulphur.

Owing to their biological activity the following individual compounds of the formula Ia' according to the invention are preferred:

3-(b-4-methylaminocarbonyloxyphenyl)-5-trifluoromethyl-1,2,4-oxadiazole;
3-(4-isopropylaminocarbonyloxyphenyl)-5-trifluoromethyl-1,2,4-oxadiazole;
3-(4-ethylaminocarbonyloxyphenyl)-5-trifluoromethyl-1,2,4-oxadiazole;
3-(4-allylaminocarbonyloxyphenyl)-5-trifluoromethyl-1,2,4-oxadiazole;
3-[4-(2-chloro-4-trifluoromethylphenoxy)-phenyl]-5-trifluoromethyl-1,2,4-oxadiazole;
3-[methoxy-(methyl)-aminocarbonyloxyphenyl]-5-trifluoromethyl-1,2,4-oxadiazole;
3-(4-hexanoyloxyphenyl)-5-trifluoromethyl-1,2,4-oxadiazole;
3-[4-(phenylaminocarboxy)-phenyl]-5-trifluoromethyl-1,2,4-oxadiazole;
3-[4-(2-methyl-3-chlorophenylaminocarboxy)-phenyl]-5-trifluoromethyl-1,2,4-oxadiazole;
3-[4-(3-ethylphenylaminocarboxyphenyl)]-5-trifluoromethyl-1,2,4-oxadiazole.

Preferred compounds of the formula I'' are those that fall under the formula Ia''

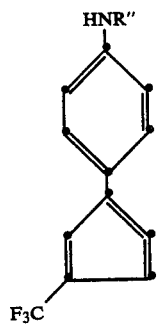

in which
R'' represents the groups C(O)NR$_1$''(R$_2$''), C(S)NR$_1$''(R$_2$''), COOR$_3$'', COSR$_3$'' or COR$_3$'', in which
R$_1$'' represents C$_1$–C$_4$-alkyl, C$_1$–C$_4$-alkoxy or aryl;
R$_2$'' represents hydrogen or C$_1$–C$_4$-alkyl and
R$_3$'' represents C$_1$–C$_9$-alkyl, C$_1$–C$_4$-haloalkyl, C$_3$–C$_4$-alkenyl or aryl.

Also preferred are compounds of the formula Ia'' that have the following substituents or combinations of these substituents with one another:
R'' represents C(O)NR$_1$''(R$_2$''), C(S)R$_1$''(R$_2$''), COOR$_3$'', COSR$_3$'' or COR$_3$'', in which R$_1$'' represents C$_1$–C$_2$-alkyl, C$_1$–C$_2$-alkoxy or phenyl, R$_2$'' represents hydrogen or C$_1$–C$_2$-alkyl and R$_3$'' represents C$_1$–C$_3$-alkyl, C$_1$–C$_2$-haloalkyl, C$_3$–C$_4$-alkenyl or phenyl.

Also preferred are compositions whose active ingredients are compounds of the formula I'' that have the following substituents or combinations of these substituents:
R'' represents C(O)NR$_1$''(R$_2$''), C(S)NR$_1$''(R$_2$''), COR$_3$'', COOR$_3$'' or COSR$_3$'', in which R$_1$'' represents C$_1$–C$_2$-alkyl, C$_1$–C$_2$-alkoxy or phenyl, R$_2$'' represents hydrogen or C$_1$–C$_2$-alkyl and R$_3$'' represents C$_1$–C$_3$-alkyl, C$_1$–C$_2$-haloalkyl, C$_3$–C$_4$-alkenyl or phenyl.

Owing to their biological activity, the following individual compounds according to the invention are preferred:

3-[4-(3-methyl-3-methoxyureido)-phenyl]-5-tri-
fluoromethyl-1,2,4-oxadiazole;
3-[4-(3,3-dimethylureido)-phenyl]-5-trifluoromethyl-
1,2,4-oxadiazole;
3-(4-methoxycarbonylaminophenyl)-5-trifluoromethyl-
1,2,4-oxadiazole;
3-(4-ethoxycarbonylaminophenyl)-5-trifluoromethyl-
1,2,4l -oxadiazole;
3-(4-isopropoxycarbonylaminophenyl)-5-trifluorometh-
yl-1,2,4-oxadiazole;
3-(4-phenyloxycarbonylaminophenyl)-5-trifluorometh-
yl-1,2,4-oxadiazole;
3-(4-acetylaminophenyl)-5-trifluoromethyl-1,2,4-
oxadiazole;
3-(4-allyloxycarbonylaminophenyl)-5-trifluoromethyl-
1,2,4-oxadiazole;
3-[4-(2-chloroethoxycarbonylamino)-phenyl]-5-tri-
fluoromethyl-1,2,4-oxadiazole;
3-[4-(3-methylthioureido)-phenyl]-5-trifluoromethyl-
1,2,4-oxadiazole;
3-[4-(3,3-dimethylthioureido)-phenyl]-5-tri-
fluoromethyl -1,2,4-oxadiazole;
3-[4-(3-methyl-3-methoxythioureido)-phenyl]-5-tri-
fluoromethyl-1,2,4-oxadiazole;
3-(4-ethylthiocarbonylaminophenyl)-5-trifluoromethyl-
1,2,4-oxadiazole;
3-(4-ethylcarbonylaminophenyl)-5-trifluoromethyl-
1,2,4-oxadiazole;
3-(4-chloromethylcarbonylaminophenyl)-5-tri-
fluoromethyl-1,2,4-oxadiazole.

Owing to their biological activity, the following compounds are preferred as active ingredients of compositions according to the invention:
3-[3-(3,3-dimethylureido)-phenyl]-5-trifluoromethyl-
1,2,4-oxadiazole;
3-[3-(3-methyl-3-methoxyureido)-phenyl]-5-tri-
fluoromethyl-1,2,4-oxadiazole;
3-[3-(3-methylureido)-phenyl]-5-trifluoromethyl-1,2,4-
oxadiazole;
3-(3-ethoxycarbonylaminophenyl)-5-trifluoromethyl-
1,2,4-oxadiazole;
3-(3-chloromethoxycarbonylaminophenyl)-5-tri-
fluoromethyl-1,2,4-oxadiazole;
3-(3-methoxycarbonylaminophenyl)-5-trifluoromethyl-
1,2,4-oxadiazole;
3-(3-isopropoxycarbonylaminophenyl)-5-trifluorometh-
yl-1,2,4-oxadiazole;
3-(3-phenoxycarbonylaminophenyl)-5-trifluoromethyl-
1,2,4-oxadiazole;
3-(3-allyloxycarbonylaminophenyl)-5-trifluoromethyl-
1,2,4-oxadiazole;
3-[3-(2-chloroethoxycarbonylamino)-phenyl]-5-tri-
fluoromethyl-1,2,4-oxadiazole.

The compounds of the formula I are prepared in the following manner:

1. Compounds of the formula I'

An oxime derivative of the formula II'

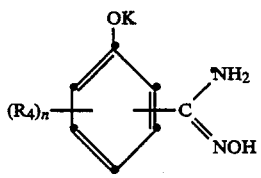

(II')

is reacted with trifluoroacetic anhydride to form a phenol derivative of the formula Ib'

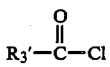

(IIIb')

which is then reacted for further substitution 1.1 with a carbamoyl chloride of the formula III'

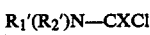 (III')

or 1.2 with a chloroformic acid ester of the formula IIIa'

 (IIIa')

or 1.3 with a carboxylic acid chloride of the formula IIIb'

 (IIIb')

or 1.4 with dialkyl sulphate or alkyl halide, preferably alkyl bromide or alkyl iodide, having from 1 to 4 carbon atoms in the alkyl groups, in the presence of a base as acid acceptor, in which X represents oxygen or sulphur and $R_1'$, $R_2'$, $R_3'$, $R_4$ and n have the meanings given under formula I, or 1.5 an oxime derivative of the formula IIa'

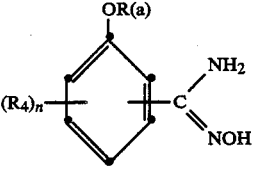 (IIa')

is reacted with trifluoroacetic anhydride to form a phenol derivative of the formula Ic'

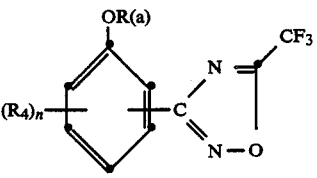 (Ic')

in which R(a) represents aryl or substituted aryl and $R_4$ and n have the meanings given under formula I.

2. Compounds of the formula I''

An aniline derivative of the formula II''

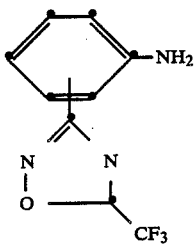

(II″)

is reacted 2.1 with a carbamoyl chloride of the formula III″

$$R_1''(R_2'')N-CXCl \qquad (III'')$$

or 2.2 with a chloroformic acid ester of the formula IIIa″

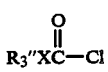

(IIIa″)

or 2.3 with a carboxylic acid chloride of the formula IIIb″

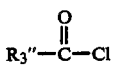

(IIIb″)

in an inert solvent in the presence of a base as acid acceptor or 2.4 with an isocyanate derivative of the formula IV $$R_1''-N=C=X \qquad (IV)$$

in an inert solvent,
in which X represents oxygen or sulphur and $R_1''$, $R_2'''$ and $R_3'$ have the meanings given under formula I″.

In the process variants (1.1) to (1.4) and (2.1) to (2.3), it is possible to use as base any suitable acid-binding agent, such as an amine, especially a tertiary amine, and also alkali metal and alkaline earth metal compounds. There may be mentioned as examples the hydroxides, oxides and carbonates of lithium, sodium, potassium, magnesium, calcium and barium, also other basic compounds, such as trimethylamine, triethylamine, tripropylamine, tributylamine, tribenzylamine, tricyclohexylamine, triamylamine, trihexylamine, N,N-dimethylaniline, N,N-dimethyltoluidine, N,N-dimethyl-p-aminopyridine, N-methylpyrrolidine, N-methylpiperidine, N-methylimidazole, N-methylpyrrole, N-methylmorpholine, N-methylhexamethyleneimine, pyridine, quinoline, α-picoline, β-picoline, isoquinoline, pyrimidine, acridine, N,N,N′,N′-tetramethylethylenediamine, N,N,N′,N′-tetraethylethylenediamine, quinoxaline, N-propyldiisopropylamine, N,N-dimethylcyclohexylamine, 2,6-lutidine, 2,4-lutidine and triethylenediamine.

In process variants (1.1) to (1.5) and (2.1) to (2.4) inert solvents and diluents are used to suit the particular reaction conditions. There may be mentioned as examples: halohydrocarbons, especially chlorohydrocarbons, such as tetrachloroethylene, tetrachloroethane, dichloropropane, methylene chloride, dichlorobutane, chloroform, chloronaphthalene, dichloronaphthalene, carbon tetrachloride, trichloroethane, trichloroethylene, pentachloroethane, difluorobenzene, 1,2-dichloroethane, 1,1-dichloroethane, 1,2-cis-dichloroethylene, chlorobenzene, fluorobenzene, bromobenzene, iodobenzene, dichlorobenzene, dibromobenzene, chlorotoluene and trichlorobenzene; ethers, such as ethyl propyl ether, methyl tert.-butyl ether, n-butyl ethyl ether, di-n-butyl ether, diisobutyl ether, diisoamyl ether, diisopropyl ether, anisole, phenetole, cyclohexyl methyl ether, diethyl ether, ethylene glycol dimethyl ether, tetrahydrofuran, dioxan, thioanisole and dichlorodiethyl ether; nitrohydrocarbons, such as nitromethane, nitroethane, nitrobenzene, chloronitrobenzene and o-nitrotoluene; nitriles, such as acetonitrile, butyronitrile, isobutyronitrile, benzonitrile and m-chlorobenzonitrile; aliphatic or cycloaliphatic hydrocarbons, such as heptane, pinane, nonane, cymol, petroleum fractions within a boiling range of from 70° to 190° C., cyclohexane, methylcyclohexane, Decalin, petroleum ether, hexane, ligroin, trimethylpentane, 2,3,3-trimethylpentane and octane; esters, such as ethyl acetate, ethyl acetoacetate and isobutyl acetate; amides, for example formamide, methylformamide and dimethylformamide; ketones, such as acetone and methyl ethyl ketone, and, if appropriate, also water. Mixtures of the mentioned solvents and diluents are also suitable.

The reaction temperatures in process variants (1.1) to (1.5) are from 0° to 180° C., preferably from 40° to 120° C., and, specifically in variant (1.4), from 0° to 100° C., preferably from 20° to 80° C., and in process variants (2.1) to (2.4) from 20° to 180° preferably from 40° to 120° C.

Some of the active ingredients covered by formula I are known from German Offenlegungsschrift No. 28 01 509. In that publication they are proposed as active ingredients of herbicidal compositions.

Surprisingly, it has been found that the compounds of formula I of this invention have, for practical field application purposes, a very advantageous microbicidal spectrum against phytopathogenic fungi and bacteria. Compounds of formula I have very advantageous curative, systemic and, in particular, preventive properties, and can be used for protecting numerous cultivated plants. With the compounds of formula I it is possible to inhibit or destroy the microorganisms which occur in plants or in parts of plants (fruit, blossoms, leaves, stems, tubers, roots) in different crops of useful plants, while at the same time the parts of plants which grow later are also protected from attack by such microorganisms.

The compounds of formula I are effective against the phytopathogenic fungi belonging to the following classes: *Fungi imperfecti* (e.g. Botrytis, Helminthosporium, Fusarium, Septoria, Cercospora, Pyricularia, Alternaria); Basidiomycetes (e.g. the genera Hemileia, Rhizocotonia, Puccinia); and, in particular, against the class of the Ascomycetes (e.g. Venturia, Podosphaera, Erysiphe, Monilinia, Uncinula). In addition, the compounds of formula I have a systemic action. They can also be used as dressing agents for protecting seeds (fruit, tubers, grains) and plant cuttings against fungus infections as well as against phytopathogenic fungi which occur in the soil.

Apart from their microbicidal activity, the compounds of formula I have nematocidal properties which make them especially suitable for controlling plant nematodes. For this utility, the compositions of the invention can be used curatively, preventively or systemically. They exhibit a broad range of activity against the various species of nematode and therefore satisfy the requirements of practice.

In the rates of application indicated below, the compounds of the invention, and also the compounds proposed in DE-OS 28 10 509, are especially well tolerated by plants.

Accordingly, the invention also relates to microbicidal compositions as well as to the use of the compounds of formula I for controlling phytopathogenic microorganisms, in particular phytopathogenic fungi, or for protecting plants from attack by said microorganisms.

The invention further embraces the preparation of agrochemical compositions, which comprises homogeneously mixing the active ingredient with one or more compounds or groups of compounds described herein. The invention furthermore relates to a method of treating plants, which comprises applying thereto the compounds of formula I or the novel compostions.

Target crops to be protected within the scope of the present invention comprise e.g. the following species of plants: cereals (wheat, barley, rye, oats, rice, sorghum and related crops), beet (sugar beet and fodder beet), pomes, drupes and soft fruit (apples, pears, plums, peaches, almonds, cherries, strawberries, raspberries and blackberries), leguminous plants (beans, lentils, peas, soybeans), oil plants (rape, mustard, poppy, olives, sunflowers, coconut, castor oil plants cocoa beans, groundnuts), cucumber plants (cucumber, marrows, melons), fibre plants (cotton, flax, hemp, jute), citrus fruit (oranges, lemons, grapefruit, mandarins), vegetables (spinach, lettuce, asparagus, cabbages, carrots, onions, tomatoes, potatoes, paprika), lauraceae (avocados, cinnamon, camphor), or plants such as maize, tobacco, nuts, coffee, sugar cane, tea, vines, hops, bananas and natural rubber plants, as well as ornamentals (flowers, shrubs, deciduous trees and conifers). This recitation constitutes no limitation.

The compounds of formula I are normally applied in the form of compositions and can be applied to the crop area or plant to be treated, simultaneously or in succession, with further compounds. These compounds can be both fertilisers or micronutrient donors or other preparations that influence plant growth. They can also be selective herbicides, insecticides, fungicides, bactericides, nematicides, mollusicides or mixtures of several of these preparations, if desired together with further carriers, surfactants or application promoting adjuvants customarily employed in the art of formulation.

Suitable carriers and adjuvants can be solid or liquid and correspond to the substances ordinarily emloyed in formulation technology, e.g. natural or regenerated mineral substances, solvents, dispersants, wetting agents, tackifiers, thickeners, binders or fertilisers.

A preferred method of applying a compound of formula I, or an agrochemical composition which contains at least one of said compounds, is foliar application. The number of applications and the rate of application depend on the risk of infestation by the corresponding pathogen (species of fungus). However, the compound of formula I can also penetrate the plant through the roots via the soil (systemic action) by impregnating the locus of the plant with a liquid formulation, or by applying the compounds in solid form to the soil, e.g. in granular form (soil application). The compounds of formula I may also be applied to seeds (coating) by impregnating the seeds either with a liquid formulation containing a compound of formula I, or coating them with a solid formulation. In special cases, further types of application are also possible, e.g. selective treatment of the plant stems or buds.

The compounds of formula I are used in unmodified form or, preferably, together with the adjuvants conventionally employed in the art of formulation, and are therefore formulated in known manner to emulsifiable concentrates, coatable pastes, directly sprayable or dilutable solutions, dilute emulsions, wettable powders, soluble powders, dusts, granulates, and also encapsulations in e.g. polymer substances. As with the nature of the compositions, the methods of application, such as spraying, atomising, dusting, scattering, coating or pouring, are chosen in accordance with the intended objectives and the prevailing circumstances. Advantageous rates of application are normally from 50 g to 5 kg of active ingredient (a.i.) per hectare, preferably from 100 g to 2 kg a.i./ha, most preferably from 200 g to 600 g a.i./ha.

The formulations, i.e. the compositions, preparations or mixtures containing the compound (active ingredient) of formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils such as epoxidised coconut oil, sunflower oil or soybean oil; or water.

The solid carriers used e.g. for dusts and dispersible powders, are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues. Particularly advantageous application promoting adjuvants which are able to reduce substantially the rate of application are also natural (animal or vegetable) or synthetic phospholipids of the series of the cephalins and lecithins, e.g. phosphatidyl ethanolamine, phosphatidyl serine, phosphatidyl glycerol, lysolecithin, plasmalogenes or cardiolipin, which can be obtained e.g. from animal or plant cells, in particular from the brain, heart, liver, egg yolkes or soybeans. Examples of useful physical forms are phosphatidyl choline mixtures. Examples of synthetic phospholipids are dioctanoylphosphatidyl choline and dipalmitoylphosphatidyl choline.

Depending on the nature of the compound of formula I to be formulated, suitable surface-active compounds are non-ionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyllaurin salts.

More frequently, however, so-called synthetic surfactants are used, especially fatty sulfonates, fatty sulfates, sulfonated benzimidazole derivatives or alkylsulfonates.

The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethyleneethanol, polyethylene glycol and octylphenoxypolyethoxyethanol. Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated alkyl, benzyl or hydroxy-lower alkyl radicals. The salts are preferably in the form of halides, methylsulfates or ethylsulfates, e.g. stearyltrimethylammonium chloride or benzyldi-(2-chloroethyl)ethylammonium bromide.

The agrochemical compositions usually contain 0.1 to 99% by weight, preferably 0.1 to 95% by weight, of a compound of formula I, 99.9 to 1% by weight, preferably 99.8 to 5% by weight, of a solid or liquid adjuvant, and 0 to 25% by weight, preferably 0.1 to 25% by weight, of a surfactant.

Whereas commercial products will preferably be formulated as concentrates, the end user will normally employ dilute formulations.

The compositions may also contain further auxiliaries such as stabilisers, antifoams, viscosity regulators, binders, tackifiers as well as fertilisers or other active ingredients for obtaining special effects.

Such agrochemical compositions constitute an object of the present invention.

The following non-limitative Examples serve to illustrate the invention in more detail.

1. PREPARATORY EXAMPLES

Example 1.1

(a) Preparatory of

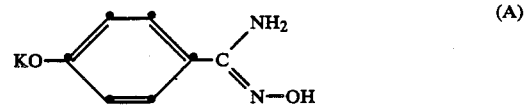

65.5 g (0.55 mol) of 4-hydroxybenzonitrile and 133.8 g of hydroxylamine hydrochloride are added to 600 ml of 80% ethanol and then 296.5 g (2.145 mol) of potassium carbonate are added in portions over a period of 20 minutes. The reaction mixture is stirred for 12 hours under reflux, cooled to room temperature and filtered. The filter cake is washed with hot ethanol and the filtrate is concentrated by evaporation. The bright red substance is digested with acetone, filtered off and dried. 79.6 g (=76.1% of the theoretical yield) of the title compound (A) having a melting point of 158°–160° C. are obtained.

(b) Preparation of

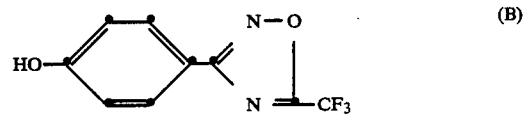

152.2 g (0.8 mol) of compound (A) are suspended in 1.5 liters of tetrahydrofuran, and 170 ml (~1.2 mol) of trifluoroacetic anhydride are added dropwise thereto over a period of 1 hour, the suspension dissolving during the exothermic reaction. The internal temperature is maintained at approximately 40° C. by cooling. The reaction mixture is then stirred for 2 hours at room temperature and poured into ice-water. The oil that separates out is extracted with toluene/ethyl acetate. The oily residue crystallises out on being left to stand. 102.9 g (47.4% of the theoretical yield) of the title compound (B) having a melting point of 66°–73° C. are obtained.

(c) Preparation of

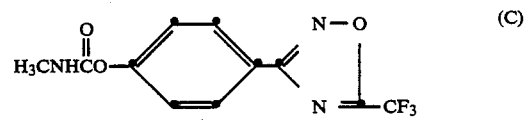

46 g (0.2 mol) of compound (B) are added, together with 0.5 g of triethylenediamine, to 300 ml of toluene. 23 ml of methyl isocyanate are added dropwise at room temperature (reaction slightly exothermic) and complete dissolution takes place. After stirring for approximately 15 minutes, the reaction product begins to precipitate and the temperature rises to 30° C. After completing the stirring operation overnight, 170 ml of cyclohexane are added and then filtration is carried out. 55.4 g (96.5% of the theoretical yield) of the title compound having a melting point of 180°–185° C. are obtained.

Example 1.2

Preparation of

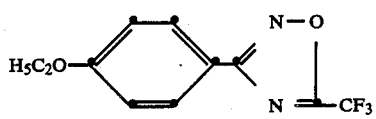

13.8 g (0.06 mol) of 3-(4-hydroxyphenyl)-5-trifluoromethyl-1,2,4-oxadiazole are added to 100 ml of 2-butanone, and then 9.9 g (0.072 mol) of potassium carbonate are added. 8.6 ml (0.066 mol) of diethyl sulphate are added dropwise thereto. The suspension is stirred for 18 hours at 80° C. and, after cooling to room temperature, is filtered. After distilling off the solvent, there are obtained 13.7 g of a yellow oil which crystallises on being left to stand. M.p. 48°–51° C.

Example 1.3

(a) Preparation of

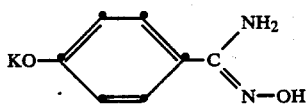

148.1 g (1 mol) of 4-nitrobenzonitrile are added, togetherwith 139 g (2 mol) of hydroxylamine hydrochloride, to 1300 ml of methanol. 80 g (2 mol) of sodium hydroxide are added thereto in portions over a period of 20 minutes (exothermic reaction). The yellow suspension is heated at reflux temperature for 3.5 hours and then filtered while hot. By adding ice-water the title compound (A) crystallises out.

Yield: 162.9 g (=89.9% of the theoretical yield). M.p. 168°–170° C.

(b) Preparation of

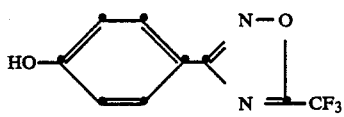

74.3 g (0.41 mol) of compound (A) are dissolved in 1400 ml of tetrahydrofuran, and then 98.3 g (0.47 mol) of trifluoroacetic anhydride are added dropwise within a period of 1 hour. The temperature rises to 35° C. After stirring for two hours at room temperature, the whole is concentrated by evaporation to half the volume, diluted with double the quantity of water and extracted with toluene/ethyl acetate. The extract is concentrated by evaporation and the residue is recrystallised from ethanol/water. Crystals of the title compound (B) are obtained.

Yield: 72.8 g (=63.5% of the theoretical yield). M.p. 62°–63° C.

(c) Preparation of

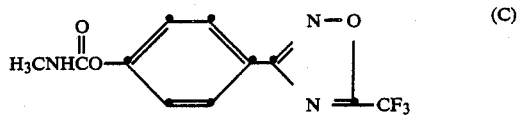

262.8 g (1.02 mol) of compound (B) are dissolved in 2200 ml of ethanol at 35° C., and a suspension of 109.2 g of ammonium chloride (2 mol) in 120 ml of water is added. 467.2 g of zinc powder (7.2 mol) are sprinkled in in portions within a period of 30 minutes and then the reaction mixture is stirred for 10 hours at reflux temperature and for a further 10 hours at room temperature. The zinc powder is filtered off and the solvent is distilled off. The resulting crude product is dissolved in toluene/ethyl acetate 1:2, insoluble secondary products are filtered off and the solution is concentrated in a rotary evaporator. The crystals which separate out are filtered off. The title compound (C) is obtained.

Yield: 142.4 g (=60.9% of the theoretical yield). M.p. 53°–58° C.

(d) Preparation of

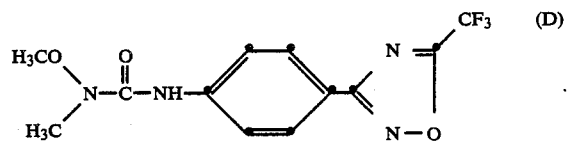

141.2 g (0.616 mol) of compound (C) are dissolved at room temperature in 480 ml of pyridine, and 135.9 g (1.1 mol) of N-methyl-N-methoxycarbamoyl chloride are added dropwise within a period of 5 minutes, the temperature rising to 53° C. After stirring for 1 hour at room temperature, the reaction mixture is poured into ice-water and filtered. The title compound (D) is obtained.

Yield: 177.4 g (=91.1% of the theoretical yield). M.p. 88°–90° C.

The compounds listed below can be prepared analogously to the Example described above.

TABLE 1

Compounds of the formula

| Comp. No. | R | R' | R'' | m.p. (°C.) |
|---|---|---|---|---|
| 1.1 | C(O)NHCH$_3$ | H | H | 180–185 |
| 1.2 | C$_6$H$_3$Cl(2)CF$_3$(4) | H | H | 59–61 |
| 1.3 | H | I | I | 110–112 |
| 1.4 | H | H | H | 68–72 |
| 1.5 | CH$_3$ | H | H | 41–44 |
| 1.6 | C(O)NCH$_3$(CH$_3$O) | H | H | 46–49 |
| 1.7 | C(O)N(CH$_3$)$_2$ | H | H | 62–66 |
| 1.8 | C(O)C$_5$H$_{11}$ | H | H | 67–69 |
| 1.9 | C(O)C$_{15}$H$_{31}$ | H | H | 62–64 |
| 1.10 | C(O)C$_7$H$_{15}$ | H | H | 42–43 |
| 1.11 | C(O)C$_9$H$_{19}$ | H | H | 35–37 |

TABLE 1-continued

Compounds of the formula

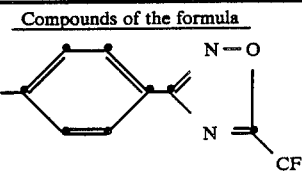

| Comp. No. | R | R' | R'' | m.p. (°C.) |
|---|---|---|---|---|
| 1.12 | C(O)C$_6$H$_{13}$ | H | H | 51–53 |
| 1.13 | C$_2$H$_5$ | H | H | 48–51 |
| 1.14 | C(O)NHCH(CH$_3$)$_2$ | H | H | 152–154 |
| 1.15 | C(O)NHC$_2$H$_5$ | H | H | 149–151 |
| 1.16 | C(O)NHCH$_2$—CH=CH$_2$ | H | H | 123–125 |
| 1.17 | C(O)NH—C$_6$H$_5$ | H | H | 133–135 |
| 1.18 | C(O)NHC$_6$H$_3$(CF$_3$)$_2$(3,5) | H | H | 141–143 |
| 1.19 | C(O)NHC$_6$H$_3$CH$_3$(2)Cl(3) | H | H | 179–181 |
| 1.20 | C(O)NHC$_6$H$_4$C$_2$H$_5$(3) | H | H | 114–116 |
| 1.21 | H | Cl | Cl | 103–110 |
| 1.22 | C(O)NHCH$_3$ | Cl | Cl | 144–145 |
| 1.23 | H | Br | Br | 96–99 |
| 1.24 | C(O)NHCH$_3$ | Br | Br | 161–165 |
| 1.25 | C(O)NHCH$_3$ | OCH$_3$ | Br | 164–167 |
| 1.26 | H | OCH$_3$ | Br | 179–182 |
| 1.27 | C(O)NHCH$_3$ | OCH$_3$ | NO$_2$ | 109–112 |
| 1.28 | H | OCH$_3$ | H | 102–103 |
| 1.29 | H | NO$_2$ | NO$_2$ | 94–97 |
| 1.30 | C(O)NHCH$_3$ | NO$_2$ | NO$_2$ | 114–116 |
| 1.31 | H | OCH$_3$ | NO$_2$ | 98–102 |
| 1.32 | C(O)NHCH$_3$ | OCH$_3$ | H | 166–168 |
| 1.33 | C(O)OCH$_3$ | H | H | 65–66 |
| 1.34 | C(O)OC$_2$H$_5$ | H | H | 48–49 |
| 1.35 | C(O)OCH(CH$_3$)$_2$ | H | H | 63–64 |
| 1.36 | C(O)SC$_2$H$_5$ | H | H | |
| 1.37 | C(S)NHCH$_3$ | H | H | |
| 1.38 | C(S)N(CH$_3$)$_2$ | H | H | |
| 1.39 | C$_6$H$_4$F(4) | H | H | |
| 1.40 | C(O)SC$_2$H$_5$ | H | H | 45–47 |
| 1.41 | C(S)N(CH$_3$)$_2$ | H | H | 92–96 |
| 1.42 | C(O)NHC$_3$H$_7$ | H | H | 130–132 |
| 1.43 | C(O)NHC(CH$_3$)$_3$ | H | H | 90–92 |
| 1.44 | C(O)NHC$_4$H$_9$ | H | H | 128–131 |

TABLE 2

Compounds of the formula

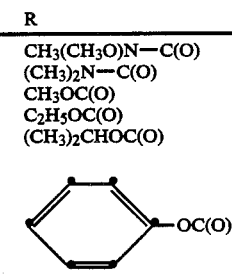

| Comp. No. | R | phys. data |
|---|---|---|
| 2.1 | H | m.p. 64–66° C. |
| 2.2 | C(O)NHCH$_3$ | m.p. 74–77° C. |
| 2.3 | C(O)OCH$_3$ | $n_D^{25,5}$ 1,4820 |
| 2.4 | C(O)OC$_2$H$_5$ | $n_D^{25}$ 1,4793 |
| 2.5 | C(O)OCH(CH$_3$)$_2$ | $n_D^{25}$ 1,4736 |
| 2.6 | C(O)SC$_2$H$_5$ | $n_D^{25}$ 1,5170 |
| 2.7 | C(S)NHCH$_3$ | |
| 2.8 | C(S)N(CH$_3$)$_2$ | m.p. 95–98° C. |
| 2.9 | C$_6$H$_4$F(4) | oil |
| 2.10 | C(O)NHC$_3$H$_7$ | m.p. 83–84° C. |
| 2.11 | C(O)NHCH(CH$_3$)$_2$ | m.p. 103–105° C. |
| 2.12 | C(O)NHC(CH$_3$)$_3$ | m.p. 103–105° C. |
| 2.13 | C(O)NHC$_4$H$_9$ | m.p. 56–58° C. |

TABLE 3

Compounds of the formula

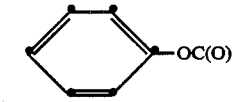

| Comp. No. | R | m.p. (°C.) |
|---|---|---|
| 3.1 | CH$_3$(CH$_3$O)N—C(O) | 88–90 |
| 3.2 | (CH$_3$)$_2$N—C(O) | 154–160 |
| 3.3 | CH$_3$OC(O) | 117–119 |
| 3.4 | C$_2$H$_5$OC(O) | 100–103 |
| 3.5 | (CH$_3$)$_2$CHOC(O) | 109–112 |
| 3.6 | 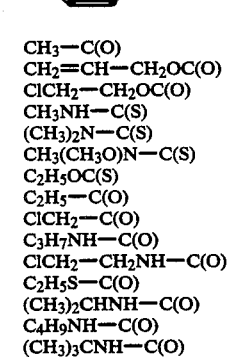 | 116–120 |
| 3.7 | CH$_3$—C(O) | 170–173 |
| 3.8 | CH$_2$=CH—CH$_2$OC(O) | 100–102 |
| 3.9 | ClCH$_2$—CH$_2$OC(O) | 115–117 |
| 3.10 | CH$_3$NH—C(S) | 148–150 |
| 3.11 | (CH$_3$)$_2$N—C(S) | 158–159 |
| 3.12 | CH$_3$(CH$_3$O)N—C(S) | 142–144 |
| 3.13 | C$_2$H$_5$OC(S) | |
| 3.14 | C$_2$H$_5$—C(O) | 159–160 |
| 3.15 | ClCH$_2$—C(O) | 143–144 |
| 3.16 | C$_3$H$_7$NH—C(O) | 212–214 |
| 3.17 | ClCH$_2$—CH$_2$NH—C(O) | 189–190 |
| 3.18 | C$_2$H$_5$S—C(O) | 133–136 |
| 3.19 | (CH$_3$)$_2$CHNH—C(O) | 211–212 |
| 3.20 | C$_4$H$_9$NH—C(O) | 172–173 |
| 3.21 | (CH$_3$)$_3$CNH—C(O) | 160–167 |

TABLE 4

Compounds of the formula

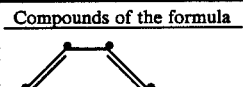

| Comp. No. | R | m.p. (°C.) |
|---|---|---|
| 4.1 | CH$_3$(CH$_3$O)N—C(O) | 74–77 |
| 4.2 | (CH$_3$)$_2$N—C(O) | 158–162 |
| 4.3 | CH$_3$NH—C(O) | 138–140 |
| 4.4 | C$_2$H$_5$—C(O) | 113–115 |
| 4.5 | ClCH$_2$—C(O) | 109–114 |
| 4.6 | CH$_3$OC(O) | 118–121 |
| 4.7 | C$_2$H$_5$OC(O) | 83–85 |
| 4.8 | (CH$_3$)$_2$CHOC(O) | 89–92 |
| 4.9 | 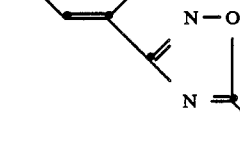 | 110–112 |
| 4.10 | CH$_2$=CH—CH$_2$OC(O) | 79–81 |
| 4.11 | ClCH$_2$—CH$_2$OC(O) | 91–93 |
| 4.12 | CH$_3$NH—C(S) | 128–131 |
| 4.13 | (CH$_3$)$_2$N—C(S) | 99–101 |
| 4.14 | CH$_3$(CH$_3$O)N—C(S) | 75–77 |
| 4.15 | C$_2$H$_5$OC(S) | |
| 4.16 | (CH$_3$)$_3$CNH—C(O) | 165–169 |
| 4.17 | C$_4$H$_9$NH—C(O) | 106–109 |
| 4.18 | (CH$_3$)$_2$CHNH—C(O) | 172–174 |
| 4.19 | C$_3$H$_7$NH—C(O) | 132–136 |
| 4.20 | ClCH$_2$—CH$_2$NH—C(O) | 121–123 |

TABLE 4-continued

Compounds of the formula

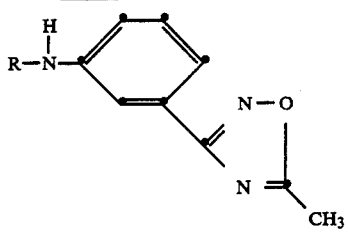

| Comp. No. | R | m.p. (°C.) |
|---|---|---|
| 4.21 | $C_2H_5S—C(O)$ | 114–116 |

2. FORMULATION EXAMPLES FOR SOLID ACTIVE INGREDIENTS OF THE FORMULA I (%=PERCENT BY WEIGHT)

| 2.1 Wettable powders | (a) | (b) | (c) |
|---|---|---|---|
| active ingredient from the Tables | 25% | 50% | 75% |
| sodium lignosulphonate | 5% | 5% | — |
| sodium lauryl sulphate | 3% | — | 5% |
| sodium diisobutylnaphthalene-sulphonate | — | 6% | 10% |
| octylphenolpolyethylene glycol ether (7–8 mol ethylene oxide) | — | 2% | — |
| highly dispersed silicic acid | 5% | 10% | 10% |
| kaolin | 62% | 27% | — |

The active ingredient is mixed well with the adjuvants and ground well in a suitable mill. Wettable powders are obtained that can be diluted with water to give suspensions of any desired concentration.

| 2.2 Emulsifiable concentrate | |
|---|---|
| active ingredient from the Tables | 10% |
| octylphenolpolyethylene glycol ether (4–5 mol ethylene oxide) | 3% |
| calcium dodecylbenzenesulphonate | 3% |
| castor oil polyglycol ether (35 mol of ethylene oxide) | 4% |
| cyclohexanone | 30% |
| xylene mixture | 50% |

Emulsions of any desired concentration can be prepared from this concentrate by dilution with water.

| 2.3 Dusts | (a) | (b) |
|---|---|---|
| active ingredient from the Tables | 5% | 8% |
| talcum | 95% | — |
| kaolin | — | 92% |

Dusts that are ready for use are obtained by mixing the active ingredient with the carriers and grinding in a suitable mill.

| 2.4 Extruder granulate | |
|---|---|
| active ingredient from the Tables | 10% |
| sodium lignosulphonate | 2% |
| carboxymethylcellulose | 1% |
| kaolin | 87% |

The active ingredient is mixed with the adjuvants, ground and moistened with water. This mixture is extruded and then dried in a stream of air.

| 2.5 Coated granulate | |
|---|---|
| active ingredient from the Tables | 3% |
| polyethylene glycol (MW 200) | 3% |
| kaolin | 94% |

(MW = molecular weight)

The finely ground active ingredient is uniformly applied in a mixer to the kaolin moistened with polyethylene glycol. A dust-free coated granulate is obtained in this manner.

| 2.6 Suspension concentrate | |
|---|---|
| active ingredient from the Tables | 40% |
| ethylene glycol | 10% |
| nonylphenolpolyethylene glycol ether (15 mol of ethylene oxide) | 6% |
| sodium lignosulphonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the adjuvants. In this manner, a suspension concentrate is obtained from which suspensions of any desired concentration can be prepared by dilution with water.

Formulation Examples for liquid active ingredients of the formula I (%=percent by weight)

| 2.7 Emulsifiable concentrates | (a) | (b) | (c) |
|---|---|---|---|
| active ingredient from the Tables | 25% | 40% | 50% |
| calcium dodecylbenzenesulphonate | 5% | 8% | 6% |
| castor oil-polyethylene glycol ether (36 mol of ethylene oxide) | 5% | — | — |
| tributylphenol-polyethylene glycol ether (30 mol of ethylene oxide) | — | 12% | 4% |
| cyclohexanone | — | 15% | 20% |
| xylene mixture | 65% | 25% | 20% |

Emulsions of any desired concentration can be prepared from such concentrates by dilution with water.

| 2.8 Solutions | (a) | (b) | (c) | (d) |
|---|---|---|---|---|
| active ingredient from the Tables | 80% | 10% | 5% | 95% |
| ethylene glycol monomethyl ether | 20% | — | — | — |
| polyethylene glycol MW 400 | — | 70% | — | — |
| N—methyl-2-pyrrolidone | — | 20% | — | — |
| epoxidised coconut oil | — | — | 1% | 5% |
| petroleum fraction (boiling range 160–190° C.) | — | — | 94% | — |

(MW = molecular weight)

The solutions are suitable for use in the form of extremely fine droplets.

| 2.9 Granulates | (a) | (b) |
|---|---|---|
| active ingredient from the Tables | 5% | 10% |
| kaolin | 94% | — |
| highly dispersed silicic acid | 1% | — |

-continued

| 2.9 Granulates | (a) | (b) |
|---|---|---|
| attapulgite | — | 90% |

The active ingredient is dissolved in methylene chloride, sprayed onto the carrier and the solvent is then evaporated off in vacuo.

| 2.10 Dusts | (a) | (b) |
|---|---|---|
| active ingredient from the Tables | 2% | 5% |
| highly dispersed silicic acid | 1% | 5% |
| talcum | 97% | — |
| kaolin | — | 90% |

Dusts that are ready for use are obtained by intimately mixing the carriers with the active ingredient.

3. BIOLOGICAL EXAMPLES

Example 3.1: Action against Puccinia graminis on wheat (a) Residual protective action Wheat plants are treated 6 days after sowing with a spray mixture (0.06% active ingredient) prepared from a wettable powder formulation of the test compound. After 24 hours the treated plants are infected with a uredospore suspension of the fungus. The infected plants are incubated for 48 hours at 95–100% relative humidity and about 20° C. and then stood in a greenhouse at about 22° C. Evaluation of rust pustule development is made 12 days after infection.

(b) Systemic action

Wheat plants are treated 5 days after sowing with a spray mixture (0.02% active ingredient, based on the volume of the soil) prepared from a wettable powder formulation of the test compound. After 48 hours the treated plants are infected with a uredospore suspension of the fungus. The plants are then incubated for 48 hours at 95–100% relative humidity and about 20° C. and then stood in a greenhouse at about 22° C. Evaluation or rust pustule development is made 12 days after infection.

Compounds of the Tables exhibit good activity against Puccinia fungi. The Puccinia attack was inhibited almost completely by compounds 1.1, 3.1, 3.12 and 4.2 (attack=0–10%) and inhibited 80–90% by compounds 1.14, 1.15, 1.16, 1.18, 1.41, 1.42, 1.43, 2.2, 2.11 and 3.2. On the other hand, Puccinia attack is 100% on untreated and infected control plants.

Example 3.2: Action against Cercospora arachidicola on groundnut plants

Residual protective action

Groundnut plants 10–15 cm in height are sprayed with a spray mixture (0.02% of active ingredient) prepared from a wettable powder formulation of the test comound, and infected 48 hours later with a conidia suspension of the fungus. The infected plants are incubated for 72 hours at about 21° C. and high humidity and then stood in a greenhouse until the typical leaf specks occur. Evaluation of the fungicidal action is made 12 days after infection and is based on the number and size of the specks.

Compared with untreated and infected control plants (number and size of the specks=100%), Cercospora attack on groundnut plants treated with compounds of the tables is substantially reduced. Thus compounds 1.1 and 1.2 inhibit the occurence of specks almost completely (0 to 10%).

Example 3.3: Action against Erysiphe graminis on barley (a) Residual protective action Barley plants about 8 cm in height are sprayed with a spray mixture (0.006% active ingredient) prepared from a wettable powder formulation of the test compound. The treated plants are dusted with conidia of the fungus after 3 to 4 hours. The infected barley plants are stood in a greenhouse at about 22° C. The fungus attack is evaluated after 10 days.

Compounds of the Tables exhibit good activity against Erysiphe fungi. For example, compound 1.23 inhibited Erysiphe attack almost completely (attack-=0–10%). On the other hand, Erysiphe attack is 100% on untreated and infected control plants.

Example 3.4: Residual protective action against Venturia inaequalis on apple shoots Residual protective action Apple cuttings with 10–20 cm long fresh shoots are sprayed with a spray mixture (0.02% a.i.) prepared from a wettable powder formulation of the test compound. The plants are infected 24 hours later with a conidia suspension of the fungus. The plants are then incubated for 5 days at 90–100% relative humidity and stood in a greenhouse for a further 10 days a 20°–24° C. Scab infestation is evaluated 15 days after infection.

Compounds from the Tables exhibit good activity against Venturia. For example, compound 3.12 inhibited Venturia attack almost completely (attack-=0–10%). On the other hand, attack is 100% on untreated and infected shoots.

I claim:

1. A composition for controlling phytopathogenic microorganisms or for preventing plants from being attacked by phytopathogenic microorganisms, which composition contains as active component at least one compound of the formula

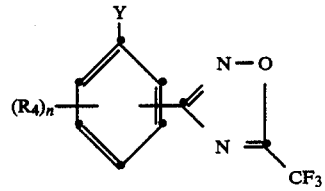

in which
Y represents OR' or HNR''
R' represents hydrogen, $C_1$–$C_4$-alkyl, phenyl, naphthyl, halophenyl, halonaphthyl, $C_1$–$C_4$-alkyl-phenyl, $C_1$–$C_4$-alkyl-naphthyl, mono-, di- or trihalomethylphenyl, mono-, di- or trihalomethylnaphthyl, mono-, di- or trihaloethylphenyl, mono-, di- or trihaloethylnaphthyl, C(X)NR$_1$'(R$_2$'), C(O)XR$_3$' or COR$_3$';
R$_1$' represents $C_1$–$C_9$-alkyl, $C_1$–$C_4$-alkoxy, $C_2$–$C_4$-alkenyl, phenyl, naphthyl, halophenyl, halonaphthyl, $C_1$–$C_4$-alkyl-phenyl, $C_1$–$C_4$-alkyl-naphthyl, mono-, di- or trihalomethylphenyl, mono-, di- or trihalomethylnaphthyl, mono-, di- or trihaloethylphenyl, or mono-, di- or trihaloethylnaphthyl, $R_2'$ represents hydrogen or $C_1$–$C_4$-alkyl;

$R_3'$ represents $C_1$–$C_{15}$-alkyl, $C_2$–$C_4$-alkyl, phenyl or naphthyl;

$R_4$ represents halogen, $C_1$–$C_4$-alkoxy or nitro; and n represents 0, 1 or 2;

X represents oxygen or sulfur;

R″ represents C(O)NR$_1$″(R$_2$″), C(S)NR$_1$″(R$_2$″), COOR$_3$″, COSR$_3$″ or COR$_3$″;

$R_1''$ represents $C_1$–$C_4$-alkyl, $C_1$–$C_4$-alkoxy, phenyl or naphthyl;

$R_2''$ represents hydrogen or $C_1$–$C_4$-alkyl and $R_3''$ represents $C_1$–$C_9$-alkyl, $C_1$–$C_4$-haloalkyl, $C_3$–$C_4$-alkenyl, phenyl or naphthyl;

provided that the radical

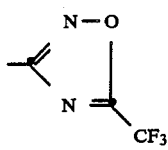

is in the 4-position of the phenyl ring when Y is HNR″;

or an acid addition salt thereof, together with a carrier.

2. A composition of claim 1, wherein Y is OR′.

3. A compound of the formula

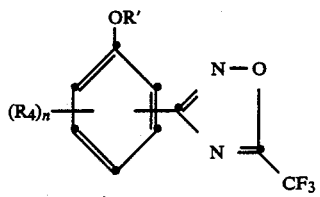

in which

R′ represents hydrogen, $C_1$–$C_4$-alkyl, phenyl, naphthyl, halophenyl, halonaphthyl, $C_1$–$C_4$-alkyl-phenyl, $C_1$–$C_4$-alkyl-naphthyl, mono-, di- or trihalomethylphenyl, mono-, di- or trihalomethylnaphthyl, mono-, di- or trihaloethylphenyl, mono-, di- or trihaloethylnaphthyl, C(X)NR$_1$′(R$_2$′), C(O)XR$_3$′ or COR$_3$′;

$R_1'$ represents $C_1$–$C_9$-alkyl, $C_1$–$C_4$-alkoxy, $C_2$–$C_4$-alkenyl, phenyl, naphthyl, halophenyl, halonaphthyl, $C_1$–$C_4$-alkyl-phenyl, $C_1$–$C_4$-alkyl-naphthyl, mono-, di- or trihalomethylphenyl, mono-, di- or trihalomethylnaphthyl, mono-, di- or trihaloethylphenyl, or mono-, di- or trihaloethylnaphthyl;

$R_2'$ represents hydrogen or $C_1$–$C_4$-alkyl;

$R_3'$ represents $C_1$–$C_{15}$-alkyl, $C_2$–$C_4$-alkenyl, phenyl or naphthyl;

$R_4$ represents halogen, $C_1$–$C_4$-alkoxy or nitro;

n represents 0, 1 or 2; and

X represents oxygen or sulfur;

or an acid addition salt thereof.

4. A compound of claim 3, wherein n is 0.

5. A compound of claim 4, in which,

R′ represents hydrogen, phenyl, halophenyl, $C_1$–$C_4$-alkyl-phenyl, mono-, di- or trihalomethylphenyl, mono-, di- or trihaloethylphenyl, C(X)NR$_1$′(R$_2$′), C(O)XR$_3$′ or COR$_3$′;

$R_1'$ represents $C_1$–$C_9$-alkyl, $C_1$–$C_4$-alkoxy, $C_2$–$C_4$-alkenyl or phenyl; and $R_3'$ represents $C_1$–$C_{15}$-alkyl, $C_2$–$C_4$-alkenyl or phenyl.

6. A compound of claim 4, in which the radical

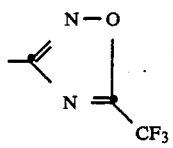

is in the 4-position of the phenyl ring, R′ represents hydrogen, phenyl, phenyl substituted by halogen or by methyl, C(X)NR$_1$′(R$_2$), C(O)XR$_3$′ or COR$_3$′, in which $R_1'$ represents $C_1$–$C_4$-alkyl, $C_1$–$C_2$-alkoxy, allyl or phenyl; $R_2'$ represents hydrogen or $C_1$–$C_2$-alkyl; and $R_3'$ represents $C_1$–$C_9$-alkyl, $C_2$–$C_4$-alkenyl or phenyl.

7. A compound of claim 4, in which the radical is in the 4-position of the phenyl ring, R′ represents hydrogen, $C_1$–$C_4$-alkyl, phenyl, halophenyl, $C_1$–$C_4$-alkyl-phenyl, mono-, di- or trihalomethylphenyl, mono-, di- trihaloethylphenyl, C(X)NR$_1$′(R$_1$′), C(O)XR$_3$′ or COR$_3$′; $R_1'$ represents $C_1$–$C_4$-alkyl, $C_1$–$C_4$-alkoxy, allyl or phenyl; and $R_3'$ represents $C_1$–$C_9$-alkyl, $C_2$–$C_4$-alkenyl or phenyl.

8. A compound of claim 4, selected from the group consisting of:

3-(4-methylaminocarbonyloxyphenyl)-5-trifluoromethyl-1,2,4-oxadiazole;

3-(4-isopropylaminocarbonyloxyphenyl)-5-trifluoromethyl-1,2,4-oxadiazole;

3-(4-ethylaminocarbonyloxyphenyl)-5-trifluoromethyl-1,2,4-oxadiazole;

3-(4-allylaminocarbonyloxyphenyl)-5-trifluoromethyl-1,2,4-oxadiazole;

3-[4-(2-chloro-4-trifluoromethylphenoxy)-phenyl]-5-trifluoromethyl-1,2,4-oxadiazole;

3-[methoxy-(methyl)-aminocarbonyloxyphenyl]-5-trifluoromethyl-1,2,4-oxadiazole;

3-(4-hexanoyloxyphenyl)-5-trifluoromethyl-1,2,4-oxadiazole;

3-[4-(phenylaminocarboxy)-phenyl]-5-trifluoromethyl-1,2,4-oxadiazole;

3-[4-(2-methyl-3-chlorophenylaminocarboxy)-phenyl]-5-trifluoromethyl-1,2,4-oxadiazole; and 3-[4-(3-ethylphenylaminocarboxyphenyl)]-5-trifluoromethyl-1,2,4-oxadiazole.

9. A composition of claim 1, wherein Y is NHR″ and n is 0.

10. A compound of the formula

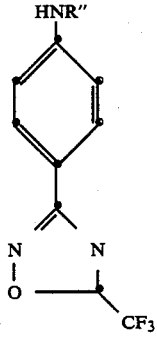

in which

R'' represents C(O)NR₁''(R₂''), C(S)NR₁''(R₂''), COOR₃'', COSR₃'' or COR₃'';
R₁'' represents C₁-C₄-alkyl, C₁-C₄-alkoxy, phenyl or naphthyl;
R₂'' represents hydrogen or C₁-C₄-alkyl and
R₃'' represents C₁-C₉-alkyl, C₁-C₄-haloalkyl, C₃-C₄-alkenyl, phenyl or naphthyl.

11. A compound of claim 10, in which
R₁'' represents C₁-C₂-alkyl, C₁-C₂-alkoxy or phenyl;
R₂'' represents hydrogen or C₁-C₂-alkyl and
R₃'' represents C₁-C₃-alkyl, C₁-C₂-haloalkyl, C₃-C₄-alkenyl or phenyl.

12. A compound of claim 10 selected from the group consisting of:
3-[4-(3-methyl-3-methoxyureido)-phenyl]-5-trifluoromethyl-1,2,4-oxadiazole;
3-[4-(3,3-dimethylureido)-phenyl]-5-trifluoromethyl-1,2,4-oxadiazole;
3-(4-methoxycarbonylaminophenyl)-5-trifluoromethyl-1,2,4-oxadiazole;
3-(4-ethoxycarbonylaminophenyl)-5-trifluoromethyl-1,2,41-oxadiazole;
3-(4-isopropoxycarbonylaminophenyl)-5-trifluoromethyl-12,4-oxadiazole;
3-(4-phenyloxycarbonylaminophenyl)-5-trifluoromethyl-1,2,4-oxadiazole;
3-(4-acetylaminophenyl)-5-trifluoromethyl-1,2,4-oxadiazole;
3-(4-allyloxycarbonylaminophenyl)-5-trifluoromethyl-1,24-oxadiazole;
3-[4-(2-chloroethoxycarbonylamino)-phenyl]-5-trifluoromethyl-1,2,4-oxadiazole;
3-[4-(3-methylthioureido)-phenyl]-5-trifluoromethyl-1,2,4-oxadiazole;
3-[4-(3,3-dimethylthioureido)-phenyl]-5-trifluoromethyl-1,2,4-oxadiazole;
3-[4-(3-methyl-3-methoxythioureido)-phenyl]-5-trifluoromethyl-1,2,4-oxadiazole;
3-(4-ethylthiocarbonylaminophenyl)-5-trifluoromethyl-1,2,4-oxadiazole; and
3-(4-chloromethylcarbonylaminophenyl)-5-trifluoromethyl-1,2,4,-oxadiazole.

13. The method of claim 2 wherein the applied compound is selected from the group consisting of:
3-[3-(3,3-dimethylureido)-phenyl]-5-trifluoromethyl-1,2,4-oxadiazole;
3-[3-(3-methyl-3-methoxyureido)-phenyl]-5-trifluoromethyl-1,2,4-oxadiazole;
3-[3-(3-methylureido)-phenyl]-5-trifluoromethyl-1,2,4-oxadiazole;
3-(3-ethoxycarbonylaminophenyl)-5-trifluoromethyl-1,2,4-oxadiazole;
3-(3-chloromethoxycarbonylaminophenyl)-5-trifluoromethyl-1,2,4-oxadiazole;
3-(3-methoxycarbonylaminophenyl)-5-trifluoromethyl-1,2,4-oxadiazole;
3-(3-isopropoxycarbonylaminophenyl)-5-trifluoromethyl-1,2,4-oxadiazole;
3-(3-phenoxycarbonylaminophenyl)-5-trifluoromethyl-1,2,4-oxadiazole;
3-(3-allyloxycarbonylaminophenyl)-5-trifluoromethyl-1,2,4-oxadiazole; and
3-[3-(2-chloroethoxycarbonylamino)-phenyl]-5-trifluoromethyl-1,2,4-oxadiazole; to said plants or to the locus thereof.

14. A composition of claim 1, which contains from 0.1 to 99% of the active component, from 99.9 to 1% solid or liquid adjuvant and from 0 to 25% surfactant.

15. A composition of claim 14, which contains from 0.1 to 95% of the active component, from 99.8 to 5% solid or liquid adjuvant and from 0.1 to 25% surfactant.

16. The method of controlling phytopathogenic microorganisms on plants or of preventing cultivated plants from being attacked by said microorganisms which comprises applying a compound of claim 3 to said plants or to the locus thereof.

17. The method of controlling phytopathogenic microorganisms on plants or of preventing cultivated plants from being attacked by said microorganisms which comprises applying a compound of claim 10 to said plants or to the locus thereof.

18. A method of controlling phytopathogenic microorganisms on plants or of preventing cultivated plants from being attacked by said microorganisms, comprising the step of applying a compound of the formula in which
Y represents OR' or HNR''
R' represents hydrogen, C₁-C₄-alkyl, phenyl, naphthyl, halophenyl, halonaphthyl, C₁-C₄-alkyl-phenyl, C₁-C₄-alkyl-naphthyl, mono-, di- or trihalomethylphenyl, mono-, di- or trihalomethylnaphthyl, mono-, di- or trihaloethylphenyl, mono-, di- or trihaloethylnaphthyl, C(X)NR₁'(R₂'), C(O)XR₃' or COR₃';
R₁' represents C₁-C₉-alkyl, C₁-C₄-alkoxy, C₂-C₄-alkenyl, phenyl, naphthyl, halophenyl, halonaphthyl, C₁-C₄alkyl-phenyl, C₁-C₄alkyl-naphthyl, mono-, di- or trihalomethylphenyl, mono-, di- or trihalomethylnaphthyl, mono-, di- or trihalomethylethylphenyl, or mono-, di- or trihalomethylnaphthyl,
R₂' represents hydrogen or C₁-C₄-alkyl;
R₃' represents C₁-C₁₅-alkyl, C₂-C₄-alkyl, phenyl or naphthyl;
R₄ represents halogen, C₁-C₄-alkoxy or nitro; and
n represents 0, 1 or 2;
X represents oxygen or sulfur;
R'' represents C(O)NR₁''(R₂''), C(S)NR₁''(R₂''), COOR₃'', COSR₃'' or COR₃'';
R₁'' represents C₁-C₄-alkyl, C₁-C₄-alkoxy, phenyl or naphthyl;
R₂'' represents hydrogen or C₁-C₄-alkyl and
R₃'' represents C₁-C₉-alkyl, C₁-C₄-haloalkyl, C₃-C₄-alkenyl, phenyl or naphthyl;
or an acid addition salt thereof.

* * * * *